(12) United States Patent
Sevastyanov

(10) Patent No.: US 8,012,994 B1
(45) Date of Patent: Sep. 6, 2011

(54) METHOD FOR THE TREATMENT OF SENSORINEURAL HEARING LOSS WITH DONEPEZIL HYDROCHLORIDE (ARICEPT®)

(76) Inventor: Victor V. Sevastyanov, Yoshkar-Ola (RU)

( * ) Notice: Subject to any disclaimer, the term of this patent is extended or adjusted under 35 U.S.C. 154(b) by 1307 days.

(21) Appl. No.: 11/525,416

(22) Filed: Sep. 22, 2006

(51) Int. Cl.
*A61K 31/445* (2006.01)
(52) U.S. Cl. ......................................... 514/319
(58) Field of Classification Search ................. 514/319
See application file for complete search history.

(56) References Cited

U.S. PATENT DOCUMENTS

| | | |
|---|---|---|
| 6,458,807 B1 | 10/2002 | Pratt |
| 6,531,488 B1 | 3/2003 | Block et al. |
| 6,608,088 B1 | 8/2003 | Nicolodi et al. |
| 2004/0002517 A1 | 1/2004 | Weisman et al. |

OTHER PUBLICATIONS

Barry Strasnik and Karen K. Hoffman, Inner Ear, Genetic Sensorineural Hearing Loss. eMedicine.com, Inc. 2004.
Fred H. Bess and Larry E. Humes, Audiology. The Fundamentals. Williams & Wilkins, 1995; p. 184 and 188.
K.W. Wright. Pediatric Opthalmology for Pediatricians. Williams & Wilkins, pp. 105-106.
J.G. Nicholls, A.R. Martin, B.G. Wallace, P.A. Fuchs. From Neuron to Brain. Sinaur Associates, Inc.—4th ed., 2001, p. 375.
Ch. I. Isambaev Physiology of Nerve Growth Factor and its Role Under Some Conditions of Organism. Tashkent. Ibn Sino Publishers, 1993. p. 323.
Medication insert, Trivastan Ritardo 50 piribedil.

*Primary Examiner* — Raymond J Henley, III
(74) *Attorney, Agent, or Firm* — Richard L. Miller

(57) ABSTRACT

A method for treating sensorineural hearing loss caused by different factors, such as hyperbilirubinemia, birth injuries, viral and bacterial infections, ototoxic medications, Usher's syndrome, craniocerebral trauma with a fracture of the base of the scull and the pyramid of the temporal bone, and neurinomas. The method includes administering donepezil hydrochloride (ARICEPT®) in a dosage of 2.5 to 5 mg for an adult, one to two times a day, for 3 to 15 courses of treatment of 20-25 days each. For a child, the dosage is reduced to a range of 0.625 to 1.25 mg.

8 Claims, No Drawings

METHOD FOR THE TREATMENT OF SENSORINEURAL HEARING LOSS WITH DONEPEZIL HYDROCHLORIDE (ARICEPT®)

1. BACKGROUND OF THE INVENTION

A. Field of the Invention

The embodiments of the present invention relate to a method for treating hearing loss, and more particularly, the embodiments of the present invention relate to a method for treating sensorineural hearing loss due to various causes by using donepezil hydrochloride (ARICEPT®).

B. Description of the Prior Art

Hearing loss is an insidious handicap that has no social barriers. The limitations imposed by the condition often are not tolerated and are poorly understood.

Hearing impairment affects up to 30% of the international community and an estimated 70 million people are deaf in the world. Sensorineural hearing loss appears to occur twice as often in developed countries in comparison to underdeveloped countries. 1.2 out of 1000 children have bilateral sensorineural hearing loss of at least 50 decibels.

Twenty-one million people in the U.S. are estimated to be hearing impaired, including approximately 1% who are deaf. An estimated 4000 infants, who are hearing impaired and another 37,000 children with milder degrees of hearing loss, are born in the U.S. each year. Recent analysis suggests that up to 6 of every 1000 infants born will have some degree of hearing impairment.[1]

[1] Barry Strasnik and Karen K. Hoffman. Inner Ear, Genetic Sensorineural Hearing Loss. eMedicine.com, Inc. 2004.

The majority of the deaf patients are people with sensorineural hearing loss. The current treatment of such patients is ineffective. The only way for their social rehabilitation is audioprosthetics. Development of new methods of treatment and rehabilitation is required in order to offer comprehensive service to people with hearing loss and their families. Pediatricians, audiologists, neurologists, speech-language pathologists, educational specialists, and otolaringologists must share in the direction of these efforts.

Sensorineural hearing loss is caused by different pathological processes. It appears as a consequence of the damage to the internal ear, cochlea, external auditory hair cells, and other cochlear structures, such as the fibers of the auditory nerve as a result of ototoxic and infectious (bacterial and viral) impact, vascular disorders in the vertebrobasilar system with a damage to central and peripheral areas of cranial nerve VIII, craniocerebral trauma with basilar skull fractures and fractures of the pyramid of the temporal bone, tumors (neurinomas) of CN VIII, tumors of the cerebellopontine angle, etc.

A number of complications can arise prior to birth, during the birth process, or soon after birth causing hearing loss. These conditions for newborns include family history of hearing loss, congenital infections (e.g. rubella), craniofacial anomalies, low birth weight, hyperbilirubinemia, ototoxic medications, bacterial meningitis, severe depression at birth (Apgar scores=0-4 at 1 min; 0-6 at 5 min), prolonged medical ventilation, stigmata, or other findings associated with a syndrome known to include a sensorineural and/or conductive hearing loss.[2]

[2] See Fred H. Bess and Larry E. Humes. Audiology. The Fundamentals. Williams &Wilkins, 1995; p. 184.

It is generally considered that nerve cells are not able to regenerate. But some researches including the applicant argue that under certain conditions nerve cells can be restored leading to a partial recovery of visual and auditory functions, which are interconnected.

25 years ago, applicant conducted a study of a small group of blind mute and deaf children (3 patients) at the age of 7-9 years old. There was an attempt to restore their visual function using galanthamine hydrobromide solution at the dosage of 0.1 ml of 0.5% of galanthamine hydrobromide for each year of life. The course of treatment included 15-20 injections. After the treatment was conducted, one of the patients manifested a minor improvement of auditory function. This finding gave an impetus to conduct additional research into the restoration of auditory function using acetylcholinesterase inhibitors in conjunction with laser stimulation.

(1) Hyperbilirubinemia.

Hyperbilirubinemia is one of the high risk factors for developing sensorineural hearing loss. Hyperbilirubinemia is a very complex metabolic complication that is thought to result from the production of too much bilirubin or the inability of the system to clear the bilirubin from the blood by the liver. It occurs when the bilirubin concentration in the blood exceeds 6-8 mg/dl. Once this level is reached, the child's skin becomes yellowish, a condition sometimes referred to as jaundice.[3]

[3] Id.

(2) Viral and Bacterial Diseases.

Severe viral and bacterial infections can result in varying degrees and patterns of sensorineural hearing loss. Infectious disease can be transmitted to the child by the mother in utero, a condition referred to as prenatal, congenital, or sometimes perinatal disease. A disease can also be acquired later in life, and is usually referred to as a postnatal condition. Many of prenatal diseases are considered a high-risk factor for hearing loss.

(3) Toxoplasmosis.

Toxoplasmosis is a disease caused by an organism (*Toxoplasma gondii*) that is transmitted to the child via the placenta. It is thought that the infection is contracted by eating uncooked meat or making contact with feces of cats. About 17% of infected newborns exhibit sensorineural hearing loss. The hearing loss is typically moderate and progressive.

Several postnatal infections produce sensorineural hearing loss. The cochlear damage produced by these viral or bacterial infections appears to be a result from the infecting agent entering the inner ear through the blood supply and nerve fibers.

(4) Sensorineural Hearing Loss Caused by Bacterial Meningitis.

Hearing loss is the most common consequence of acute meningitis. Although the pathways used by the organisms to reach the inner ear are not altogether clear, several routes have been suggested. These include the bloodstream, the auditory nerve, and the fluid supply of the inner ear and the middle ear. The prevalence of severe-to-profound sensorineural hearing loss among patients with this disorder is about 10%. Another 16% will exhibit transient conductive hearing loss. Interestingly, some patients with sensorineural hearing loss will exhibit partial recovery, although such findings are rare.[4]

[4] See Fred H. Bess and Larry E. Humes. Audiology. The Fundamentals. Williams &Wilkins, 1995; p. 188.

(5) Sensorineural Hearing Loss Caused by Ototoxic Drugs.

A negative side effect of some antibiotic drugs is the production of the severe high-frequency sensorineural hearing loss. A group of antibiotics known as aminoglycosides are particularly hazardous. This group, also commonly referred to as the "mycin" drugs, includes streptomycin, neomycin, kanamicin, and gentamicin. A variety of factors can determine whether hearing loss is produced in a specific patient. These factors include the drug dosage, the susceptibility of the patient, and the simultaneous or previous use of other ototoxic agents.

Ototoxic antibiotics reach the inner ear through the bloodstream. The resulting damage is greater in the base of the cochlear. Outer hair cells are typically the primary targets, with only limited damage appearing in other cochlear structures. This results in an audiometric pattern of moderate-to-severe high-frequency sensorineural hearing loss in both ears.

Some ototoxic drugs cause a temporary or reversible hearing loss. Perhaps the most common such substance is aspirin. When taken in large amounts, aspirin can produce a mild-to-moderate temporary sensorineural hearing loss.

(6) Sensorineural Hearing Loss Due to Usher Syndrome.

Usher syndrome type 1 (USH-1) is an autosomal recessive disease characterized by profound hearing impairment, absent vestibular function, and progressive loss of vision due to retinitis pigmentosa.

Owing to the severe handicap of the combined disorders, early diagnosis of USH-1 is of crucial importance. The profound hearing deficit is often detected during hearing tests in infancy. The sight problems, however, do not develop until later and diagnosis is often delayed.

The diagnosis of Usher syndrome is established by electroretinography (ERG), as a confirmation of the retinitis pigmentosa is a prerequisite.[5]

[5] K. W. Wright. Pediatric Ophthalmology for Pediatricians. Williams &Wilkins, pp 105-106.

(7) Sensorineural Hearing Loss Caused by Craniocerebral Trauma with a Fracture of the Base of the Skull and the Pyramid of the Temporal Bone.

The origin of otoneurological symptoms in this kind of trauma is very complicated, varied and multifold at different stages of the disease.

The disorders may be caused by different factors, such as by the peripheral damage to auditory and vestibular analyzers, central nervous system damage in the acute period of trauma (cortical damage, edema of the medullary substance and arachnoid membrane, minor hemorrhages especially in the vestibular section of CN VIII, etc.

In the case of craniocerebral trauma, the fracture lines from the calvarium go down to the skull base and damage the superior and posterolateral parts of the external auditory canal, middle, and inner ear.

In the case of longitudinal pyramidal fractures, bleeding from the ear may occur as a result of the rupture of the tympanic membrane and the skin of the external auditory canal. Very often patients with a longitudinal fracture develop neuropathy of the facial nerve on the side of the injury. Audiometry reveals partial loss of bone-conducting and air conducting hearing of high frequency tones (4000 to 8000 Hz).

In the case of transverse fractures of the temporal bone, which are produced by blows to the occiput, the fracture line begins in the posterior fossa at or near the foramen magnum and crosses the petrous ridge through the internal auditory canal or the optic capsule.

In the cases of transverse fractures of the temporal bone, due to automobile accidents or other causes of head injury, the labyrinth is involved more frequently than in longitudinal fractures. Severe vertigo with severe or total hearing loss is not uncommon in such injuries. In milder injuries, labyrinthine concussion may occur, with transitory auditory-vestibular symptoms. Audiometric investigation of the affected side in the acute period reveals hearing loss of a mixed type with the disturbances of both sound conducting and sound perception.

(8) Sensorineural Hearing Loss Caused by Neurinomas.

Cerebellopontine angle is a triangular area located at the junction of the cerebellum, pons and medulla.

Tumors of the cerebellopontine angle are mostly neurinomas of CN VIII, which develop from undifferentiated germinal Schwann cells, cochlear or more often vestibular nerves, situated in the inner acoustic duct. They squeeze the inner auditory artery and its branches, which produces ischemia of the inner ear and causes vestibular and hearing disorders. The tumor is normally located in one side, rarely in both sides. Most frequently occurring tumors are benign growths in the auditory nerve, referred to as acoustic neurinomas, acoustic shwannomas, acoustic neurilemoma.

The symptoms are caused by the compression or displacement of the cranial nerves, the brain stem, and the cerebellum. Trifacial (CN V) and facial nerves (CN VII) are affected most often because of their anatomical proximity to the vestibulocochlear nerve.

In research, applicant observed the development of neurinoma in patients during the period from 2 to 8 years. In the first stage, patients complained of tinnitus. In case of bilateral process the noise occurred in both ears. Then a gradual hearing loss from moderate to severe to profound was observed. In two patients, where neurinomas developed slowly, the appearance of tinnitus was not observed.

The first symptoms of neurinoma also include headaches and facial neuralgia. In the early stages, spontaneous nystagmus in the affected side maybe manifested, which is indicative of a vestibular disorder. In the case of neurinoma high frequency (2000-10 000 Hz) hearing loss is observed.

Considerable tumors cause hypertensive hydrocephalic syndrome, which can result in the loss of taste.

(9) Minimal Hearing Loss.

This is an insignificant loss of the peripheral hearing by 15-25 dB, which causes disorders of phonemic hearing. Phonemes are the basic elements of speech. The basic sounds can be analyzed as combinations of frequency-time relations. For example, a continuous component at 1000 Hz accompanied by a second component starting at 5000 Hz and descending rapidly to 500 Hz. A failure to differentiate phonemes leads to speech defects.[6]

[6] See J. G. Nichollis, A. R. Martin, B. G. Wallace, P. A. Fuchs. From Neuron to Brain. Sinaur Associates, Inc. $-4^{th}$ ed., 2001, p. 375.

There are two types of peripheral hearing loss, including bilateral or unilateral. In cases of bilateral hearing disorders, even decrease loudness in the perception of different acoustic signals is observed (i.e, phonemes, speech, music, sounds of nature).

In the case of unilateral hearing disorders, the hearing perception decreases two times compared to normal perception. Unilateral hearing loss leads to the disorders of differentiation in the sound direction and the sound localization resulting in spatial hearing disorders.

Minimal hearing disorders can be caused by infectious and viral diseases of the mother, toxicosis of pregnancy, postnatal asphyxia, intracranial birth injury, hyperbilirubinemia, hemolytic disease of newborn; prematurity (birth weight below 3.3 lb), the use of ototoxic medications by the mother during pregnancy, and genetic factors.

Minimal hearing loss in the postnatal period can arise from trauma or infections of the inner ear and the trunk of the vestibulocochlear nerve. Inflammation of the internal ear is a result of the transition of the inflammatory process from the internal ear to the arachnoid membrane (in case of meningitis and encephalitis). Also, the dissemination of the infection by the blood in the case of infectious diseases, such as mumps, measles, scarlet fever, flu, and herpes.

A frequent cause of minimal hearing loss in most children with speech pathology is a result of overgrowth of adenoid vegetations (II and III degree), old otitis, tubootitis, obturation of the auditory duct caused by the chronic inflammation of its walls due to infections or purulent discharge from the middle ear, obturation of the auditory duct by earwax, and allergic rhinitis resulting in eustachitis.

In the case of sound conducting organs disorders, i.e., damage to the auditory duct to the tympanic membrane, a child has difficulty in the perception of such sounds as buzzing, knocking, low voice, and also low frequency and medium frequency phonemes. This results in speech impediment. Such disorders hamper the acquisition language.

Sound perception disorders (first degree sensorineural hearing loss) are caused by dysfunctions of the peripheral perceiving part of the auditory analyzer (part of the labyrinth with the Organ of Corty and the vestibulocochlear nerve endings).

In the case of minimal disorders of sound perception, the ability to hear high frequency sounds (buzzing, creaking, rustling, and high frequency phonemes) is diminished. High voice registers are not perceived as well as low frequency registers, especially in a noisy environment. The perception of phonemes, words, and speech is impaired.

Combined disturbances are a result of a combination of defects of the sound conducting and the sound perception. In such cases, the perception of high frequency and low frequency phonemes is impaired.

(10) Sensorineural Hearing Loss of Vascular Genesis.

Transitory ischemic attacks or an ischemic stroke in the vertebrobasilar system are often accompanied by dizziness and ataxia. In the case of occlusion of the inner auditory artery, patients complain of central dizziness with a unilateral loss of hearing, since this artery supplies the vestibulocochlear nerve (CN VIII). The inner auditory artery can move away from the basilar artery or from the anterior inferior cerebellum artery.

Dizziness is accompanied with nistagmus, the rapid phase of which is contralateral to the affected side. Hearing loss is of the unilateral sensorineural type.

Hearing disorders can be linked to atheromatose and atherosclerotic damage to the inner auditory artery, which causes blood supply disturbance in the organ of Corty, semicircular ducts, statoconic apparatus, and secondary degenerative changes in the nerve roots of the vestibulocochlear nerve.

These changes are characterized by simultaneous occurrence of headaches and tinnitus, frequently in the morning. These symptoms are observed in patients over 50 years of age.

Isolated loss of low frequency sound perception can testify to the vascular genesis of the hearing loss, as the blood supply of the base and the apex of the cochlear is carried out by different arteries. The more frequent reason for sudden deafness is vascular ischemia of the inner ear. Hearing loss can be observed on the side of cerebral symptoms of the cervical osteochondrosis. The main symptom is diminished sound perception with the prevailing progressive hearing loss. Audiographically, the lessening of hearing is observed on the side of the cerebral symptoms of the cervical osteochondrosis.

2. SUMMARY OF THE INVENTION

It is an object of the embodiments of the present invention to provide a method for treating sensorineural hearing loss due to various causes by using donepezil hydrochloride (ARICEPT®) that avoids the disadvantages of the prior art.

Briefly stated, another object of the embodiments of the present invention is to provide a method for treating sensorineural hearing loss caused by different factors, such as prenatal and postnatal complications, damage to internal ear, cochlear, external auditory hair cells, and other cochlear structures, and the fibers of the auditory nerve as a result of ototoxic and infectious (bacterial and viral) impact, vascular disorders in the vertebrobasilar system with a damage to central and peripheral areas of cranial nerve VIII, craniocerebral trauma with basilar skull fractures and fractures of the pyramid of the temporal bone, tumors (neurinomas) of CN VIII, tumors of the cerebellopontine angle, etc. The method includes administering donepezil hydrochloride (ARICEPT®) in a dosage of 2.5-5 mg for an adult, one to two times a day, for 3-15 courses of treatment of 20-25 days each. For a child, the dosage to a range of 0.625-1.25 mg.

The novel features which are considered characteristic of the embodiments of the present invention are set forth in the appended claims. The embodiments of the present invention themselves, however, both as to their constructions and their methods of operation, together with additional objects and advantages thereof, will be best understood from the following description of the specific embodiments of the present invention.

3. DETAILED DESCRIPTION OF THE PREFERRED EMBODIMENTS

A. Example I (1) Treatment for Sensorineural Hearing Loss Caused by Hyperbilirubinemia Research was conducted on four patients (age 2 to 5 years) who had hyperbilirubinemia soon after birth. The hearing impairment was diagnosed when the children were examined and treated for hyperkinetic cerebral palsy. The children were not able to walk.

In this group, three children had a hearing loss from 71 to 75 dB and a two-year-old female patient was practically deaf with the hearing threshold over 95 dB. With the signed consent of their parents, the children were treated with ARICEPT® 0.625 mg once a day during 25 days.

After three courses of treatment, the patients manifested some decrease of hyperkinesias and their concentration improved. There was no improvement in hearing. The parents of one child refused to continue the treatment as there was no desired effect.

Two children underwent 10 courses of treatment with ARICEPT® 0.625 mg twice a day for 25 days with a three months break. After the treatment, their hearing improved by 10-15 dB.

In the female patient with the profound hearing loss, after ten courses of treatment with ARICEPT®, the hearing threshold was 90 dB. Hyperkinesia decreased and the patient began to walk. Also, there was a first attempt to fit the child with a hearing aid.

B. Example II (1) Treatment for Sensorineural Hearing Loss Caused by Birth Injury Research was conducted with 4 patients whose hearing loss was caused by birth injury. Two patients were twin boys of 10 years and two patients were 6 years old each.

The twins had sensorineural hearing loss in both ears. They were treated with ARICEPT® 2.5 mg twice a day for 20 days. The course was repeated in 1.5 months, and the third course was conducted in 3 months. The patients manifested decreased fatiguability and their speech became more understandable. In one ear the hearing improved by 10 and 15 dB.

Treatment was then conducted according to the following pattern. ARICEPT® 2.5 mg twice a day for 25 days, followed by a 7 day break, then another course of 2.5 mg twice a day for 25 days with a 7-10 day break, and one more course of ARICEPT® 2.5 mg twice a day for 25 days. To enhance the desired effect, starting with the 4$^{th}$ course of treatment, the patients received PERIBEDIL® 10 mg twice a day alongside ARICEPT®.

In each patient the hearing improved by 20-25 dB in one ear. After that the treatment was discontinued. The patients' hearing aids were tuned up to decrease the volume of the signal.

The six year old girl had a combined hearing loss of 70 dB and the other six year old male patient had sensorineural hearing loss of 65 dB. These patients were treated with ARICEPT® 2.5 mg once a day for twenty days. The courses were repeated every three months for three years. They received 8 and 10 courses respectively. In the female patient, the hearing improved by 15 dB and in the male patient by 10 dB.

C. Example III (1) Treatment for Neuropathy of cn viii of Toxic and Infectious Genesis This research involved observation of neuropathy in the vestibulocochlear nerve of 17 patients.

In two patients, the hearing loss was caused by toxoplasmosis. In one patient, inborn toxoplasmosis was diagnosed at the age of three. The other patient developed toxoplasmosis at 10 years of age from an infected cat.

Both patients had sensorineural hearing loss. After toxoplasmosis was diagnosed, a specific therapy was conducted, after which their hearing improved by 10-15 dB.

The three-year-old patient was treated with ARICEPT® 0.625 mg once a day in the morning during 20 days. The second course was conducted in three months. After four courses of treatment, his hearing improved by 25 dB.

The ten-year-old patient was treated with ARICEPT® 2.5 mg once a day in the morning for 20 days, the course was repeated in three months. After 5 courses of treatment, his hearing improved by 30 dB.

Five patients developed the condition after tuberculose meningitis. Two of the patients at the age of 6 and 12 months and three patients at the age from 5 to 7 years. The disease was diagnosed late and only after the development of the brain symptomatology, high fever, vomiting, presence of the positive meningeal symptoms. The diagnosis was confirmed by lumbar puncture and the investigation of the cerebrospinal fluid.

In these cases, the neuropathy of the auditory nerve developed as a result of the toxic influence of the infection and the effect of ototoxic influence of certain antibiotics such as streptomycin. The patients had severe to profound hearing loss. Three patients had partial optic atrophy.

The infants of 6 and 12 months old developed complete deafness. The tests showed the hearing loss with threshold perception over 95 dB. The auditory evoked potentials testified to a severe damage to the auditory nerve. With the signed consent of the parents the patients received ARICEPT® 1.25 mg twice a day. Before that there was an attempt to fit the children with hearing aids but the children refused to wear them.

The patients received 12-15 courses of treatment with ARICEPT® 1.25 mg twice a day. The second course was conducted in 1.5 months. The third course was repeated in three months according to the same pattern. And, further on every three months during 2-3 years. The first benefits were observed after the 8$^{th}$ course of treatment. The hearing improved by 5-10 dB. After this it was possible for the patients to use a hearing aid.

When treating patients with neuropathy of the auditory nerve with ARICEPT®, if no positive changes are observed after 8 courses of treatment, the treatment should be discontinued.

Out of the three patients at the age of 5-7 years, one had the hearing loss of 95 dB and the other two −60-70 dB. The patient with the profound hearing loss received three courses of treatment 1.25 mg ARICEPT® two times a day during 20 days. The next course was conducted in 1.5 months and then in three months. Because there were no positive effects, the parents refused to continue the treatment.

In the two other patients, after 3 courses of treatment with ARICEPT®, the hearing improved by 5-10 dB. It was noted that after the patients suffered a cold or flu, their hearing returned to the initial level. It was necessary to conduct from 3 to 5 courses of treatment with ARICEPT® twenty days each every three months in order to improve the hearing by 5-10 dB In 10 patients at the age of 4-5 years old sensorineural loss of hearing may be connected with the combined impact of ototoxic drugs and viral or bacterial infection. The mothers of 4 patients were administered antibiotics during their pregnancy. When the mothers were taking the drugs they complained of dizziness, which was thought to be connected with pregnancy but not one of the side effects of antibiotics. That is why the antibiotics were not withdrawn. The presented problem when the children were referred to the doctors was speech delay.

6 children suffered pneumonia at the age of 1-2 years old and were treated with kanamicin and streptomycin. After the treatment with antibiotics, the speech development of these children was impaired and the initial manifestations of speech disappeared.

All 10 patients had bilateral hearing loss. The audiogram showed impairment of high frequency tones perception. The loss of hearing was 50-70 dB. These children were refused treatment because of its ineffectiveness. The children were administered ARICEPT® 0.625 mg once a day for 20 days. The course of treatment was repeated every 3 months. They received 4 courses within a year. All in all they received up to 8 courses. The hearing improvement of 5-15 dB was observed between the third and the fifth courses. After that further courses of treatment didn't yield any improvement.

For the rehabilitation of these children, some classes comprising multimedia technologies were conducted. The children wear hearing aids.

In the case of the sensorineural hearing loss, the auditory receptor and the fibers of vestibulocohlear nerve are damaged. Applicant hypothesizes that ARICEPT® effects the processes of synaptogenesis in the auditory system and afferent innervations of the hair cells. It is likely that ARICEPT® impacts the nerve growth factor and the nerve growth factor can play the role of trophic factor for the neurons of the local cholinergic chains.[7]

[7] Ch. I. Isambaev Physiology of Nerve Growth Factor and its Role under Some Conditions of Organism. Tashkent. Ibn Sin 0 Publishers, 1993. p. 323.

D. Example IV

(1) Treatment for Sensorineural Hearing Loss Caused by Usher Syndrome

A group of 4 children of 5-6 years old with Usher's syndrome were studied. They manifested profound hearing impairment of 65-75 dB alongside progressive loss of vision due to retinitis pigmentosa. These children had been previously refused treatment on the account of their disease being genetic.

With the informed consent of their parents, the treatment with ARICEPT® 1.25 mg 2 times a day for 20 days was conducted. In 1.5 months there was an improvement in hearing by 5 dB. The second course of treatment was conducted in three months –1.25 mg ARICEPT® two times a day. The third course was conducted in three months according to the same pattern. After that the hearing improved by 10-15 dB. The children also manifested improved visual function.

After six months, two patients alongside ARICEPT® were also administered PIRIBEDIL® 5 mg two times a day. PIRIBEDIL® is a vasodilative drug used for treating vision and hearing disorders. Applicant observed that the hearing was improved by 5-10 dB. The patients were recommended to have a follow up treatment every 6 months according to the same pattern.

E. Example V

(1) Treatment for Sensorineural Hearing Loss Caused by Craniocerebral Trauma with a Fracture of the Base of the Skull and the Pyramid of the Temporal Bone Eight patients were selected for treatment with ARICEPT®. Two patients at the age of 3 and 4 years old, four people at the age of 23-25 years, and two people at the age of 45 and 50. Sensorineural loss of hearing in the patients of this group was connected with the fractures of the pyramid of the temporal bone and the fracture of the skull base.

In the children, the trauma resulted from a fall out of a window from the 7$^{th}$ and the 9$^{th}$ floors respectively. The other six patients received their injuries in car accidents. All of them were very severely traumatized people who had previously undergone neuro-surgical treatment. Each of them on average spent from 45 to 60 days in intensive care units and later they were discharged from the in-patient departments as incurable.

The two children had sensorineural loss of hearing of 70 and 75 dB. The attempt to make them wear a hearing aid failed. They had a CAT scan of the inner and middle ear. It was decided to treat the children with ARICEPT® with the signed consent of their parents.

The children received ARICEPT® 0.625 mg two times a day for 20 days. They had 4 courses of treatment within a year. After the treatment the hearing improved by 5 dB and 10 dB (60 dB and 70 dB respectively). After 8 courses of treatment with the interval of two months, the hearing improved by 10 dB and 15 dB from the initial level and became 55 dB and 65 dB respectively. When the children reached the age of 5, the dosage of ARICEPT® was increased to 1.25 mg two times a day.

In the next three years, the patients received treatment with ARICEPT® once in 6 months during 20-25 days. The hearing improved by 15-20 dB from the initial level (55 dB in both children). At the age of six, the children started to wear personal hearing aids, though not constantly. The further treatment with ARICEPT® didn't yield any results.

Especially indicative is the case of a 50-year-old patient, who had fractures of the skull, a fracture of the temporal bone, neuropathy of the facial nerve on the right side and bilateral optic atrophy. These injuries were the result of a bad car accident. The patient had undergone neurosurgery and spent a long time in an intensive care unit. When he was discharged, further treatment was considered pointless. The hearing threshold in the right ear was over 92 dB, in the left 85 dB. The patient suffered from severe depression, though before the accident he used to be a very optimistic, cheerful person, a musician.

The patient started to receive treatment with ARICEPT® 5 mg twice a day for 25 days. The course of treatment was repeated every 1.5-2 months four times a year. After 8 courses of treatment, the patient reported the improvement of hearing in the left ear by 10 dB (75 dB) and in the right ear no changes were observed. In the next 5 years, the patient received ARICEPT® once in 6 months 5 mg one time a day in the morning.

During the treatment there was an attempt to increase the dosage of ARICEPT® initially to 10 mg a day in the morning, and then to 10 mg twice a day. But the patient refused to take this dosage because of the appearance of side effects, such as agitation, irritability, sleep disturbances, and tinnitus. Henceforward, the patient received ARICEPT® 5 mg once a day in the morning during 30 days two times a year. After 5 years of treatment the hearing improved to 54 dB in the left ear. In the right ear the hearing was not restored. Apllicant also observed improvement of the visual function in the left eye. There was complete optic atrophy without light perception in the right eye. After two years of treatment, the depression was gone and he had a spiritual awakening. Later on, the treatment with ARICEPT® was terminated as there was no further improvement.

The four patients 23-25 years of age and a 45-year-old patient had a fracture of the skull base and the temporal bone, which caused sensorineural hearing loss. They received ARICEPT® 5 mg two times a day during 25 days. There was a 7-10 day break between the courses. The treatment lasted 3 months followed by a 3-month break. Then the treatment was repeated. After a year, the patients reported improvement in hearing by 5-10 dB. Further on, ARICEPT® was administered 5 mg twice a day during 30 days. The course was repeated every 6 months during 3 years. The marked improvement was observed 3 years after the beginning of the treatment by 15-25 dB and reached 50-55 dB. In the fourth year, applicant didn't observe any positive changes.

As applicant's research shows, the improvement of hearing after the first year of treatment with ARICEPT® was unstable. And, if patients contracted a cold or flu, their hearing diminished to the initial level.

The present research demonstrated that the administering of ARICEPT® in patients with craniocerebral trauma with a fracture of the skull base improves hearing up to 50-55 dB, which enables some patients to resume their usual activities and occupations.

The first few courses of treatment may appear not to show any visible improvement. But this should not be a reason for discontinuing the treatment with ARICEPT®. Only if no positive changes are observed after 8 courses of treatment with ARICEPT® should it be discontinued.

The dosage of 10 mg in applicant's research caused side effects and didn't show any marked improvement compared to the dosage of 5 mg. The treatment with ARICEPT® is especially beneficial for children, as wearing a hearing aid sometimes presents a problem for them.

F. Example VI (1) Treatment for Neurinomas

Neurinomas of CN VIII 2 patients of 15 and 35 years of age.

Neurinomas of the cerebropontine angle—7 patients (2 patients of 25 and 28 years of age and 5 people from 35 to 45 years of age).

Meningioma—2 patients (15 and 12 years of age).

Arachnoidal cyst—1 patient of 18 years of age.

(a) Neurinomas of CN VIII.

In two patients, the neurinomas of CN VIII were found after the MRI investigation of the brain and examination of brain stem auditory evoked potentials as the tumors were not large −0.4 in and 0.6 in.

The patients manifested the following symptoms. Diminished hearing, tinnitus, and the sensation of stuffiness in the ear. As the tumors are benign, the patients refused surgery. The patients were observed and investigated once a year (MRI and audiometry). They were chosen for treatment with ARICEPT®. They received ARICEPT® in the dosage of 2.5 mg twice a day during 20 days.

After the first course, they reported the diminishing of tinnitus and stuffiness in the ear. The lessening of tinnitus was noticed on the $7^{th}$ day of the treatment with ARICEPT®. The second course was conducted in three months' time in the same dosage. The third course was conducted in 6 months. MRI showed insignificant growth of the tumors. The audiometry registered some improvement in hearing by 5-10 dB. As the drug is very expensive, the patients decided not to continue the treatment with ARICEPT®. They came for a follow up visit two years later complaining of diminished hearing by 15-25 dB. MRI registered the growth of the tumor to 0.8 in. The immune status and the cytokinic status were examined, after which the correction of the immune status and the treatment with ARICEPT® 2.5 mg twice a day were conducted. After 10 days of receiving ARICEPT®, the patients reported insignificant diminishing of tinnitus, but also they observed a periodic appearance of headaches. The dosage of ARICEPT® was lowered to 1.25 mg twice a day. As the patients complained of agitation and sleep disturbances, the second course of treatment with ARICEPT® was cancelled. The patients received two more courses of treatment in three months' time −1.25 mg ARICEPT® twice a day. After the treatment, tinnitus decreased and the hearing improved by 5-10 dB. 5 years later, the patients complained of diminished hearing and dizziness. They opted not to have neurosurgery.

(b) Neurinomas of Cerebellopontine Angle.

In all 7 patients, the tumor was diagnosed late and was of a considerable size. In spite of the fact that all of them had consulted doctors, they were correctly diagnosed only after the appearance of the symptoms of damage to the facial nerve, ataxy, and complete hearing loss. Some of the patients underwent neurosurgery, including partial removal of the tumor followed by chemo- and radio-therapy. The patients manifested paralysis of the facial nerve, optic atrophy, and tinnitus, dizziness and paresis or hemisyndrom of different degrees.

After the operations, some of the patients had severe complications. The audiograms showed disorders in the perception of the high frequency tones with the descending type of the audiometric curve, i.e., the disturbances characteristic of sensorineural hearing loss. Disorders of differentiation of words, especially in noisy environments. Some patients manifested convulsions and severe headaches. The encephalogram registered readiness for convulsions. Such patients initially underwent anticonvulsant therapy with CARBAMAZEPINE® 100 mg two times a day. On the $5^{th}$-$7^{th}$ day of treatment, they received ARICEPT®, first 1.25 mg once a day, and in 5 days 1.25 mg twice a day. On the $10^{th}$ day from the beginning of the treatment with ARICEPT®, they received 2.5 mg twice a day for 20 days. In a month and a half the treatment was repeated in conjunction with the anticonvulsant therapy, ARICEPT® 2.5 mg once a day. The attempt to increase the dosage to 5 mg twice a day caused headaches and sleep disturbances. That is why applicant returned to the dosage of 2.5 mg ARICEPT® a day. This dosage didn't produce side effects.

The course of treatment was repeated every 3-6 months. After the treatment, this group of patients noticed a decrease of tinnitus and their hearing was improved by 5 to 20 dB. Applicant also observed the improvement in their visual function. The patients started to differentiate shapes of objects, which helped them to orient in the surroundings and to come to the clinic without a guide.

After 5-6 courses of treatment, there was no further improvement.

The degree of hearing improvement depended on the size of the tumor. The bigger was the tumor, the worse was the restoration of hearing.

(c) Meningiomas.

Applicant observed two patients with meningiomas. Their tumors were of a considerable size. These patients had undergone surgery, which was conducted in two stages, and was followed by chemo- and radiation therapy. These patients were practically blind, and had bilateral optic atrophy, their hearing function was impaired by 30-40 dB, they were not able to differentiate words in noisy environments. They also manifested convulsive attacks up to 15 times a day. They went through the anticonvulsant therapy, after which their convulsions occurred only for 2 times a month. With their signed consent, the patients underwent treatment with ARICEPT® in conjunction with the anticonvulsant therapy, including 1.25 mg ARICEPT® once a day during 15 days. In a month and a half, the treatment was conducted according to the following pattern. 1.25 mg once a day for 7 days, followed by a 5 day break. Then—another 7 days of treatment with ARICEPT® followed by a 5 day break, then 7 more days of ARICEPT®. This course was repeated in 3 months. The third course was conducted in 6 months. After the treatment, the patients manifested increased legibility of speech, improvement of hearing, and clear differentiation of the source of light. These improvements satisfied the patients and no further treatment was conducted.

(d) Arachnoidal Cyst.

The arachnoidal cyst in the cerebropontine angle of the brain was found in a female patient of 18 years of age after MRI and CT investigation. The manifested symptoms were headaches and dizziness. There was a decrease in hearing by 40 dB and later she developed neuropathy of CN VII. The intercranial part of the facial nerve was affected. There was muscular laxity of the forehead, eyes, and mouth. When closing the right eye, the eyeball rolled up.

Previously, the patient had been treated conservatively including corticosteroids.

The treatment hadn't brought any improvement in the patient's condition. She still had persistent headaches and her right eye was watering. Because the right mouth angle was immobile, she experienced a certain inconvenience when eating.

She was chosen for the treatment with ARICEPT® 2.5 mg twice a day. She also received CARBAMAZEPINE® 200 mg two times a day. The first course of treatment lasted twenty five days. The second course was conducted after a month and a half, including 2.5 mg ARICEPT® twice a day for 25 days. After the treatment, the eyel was closing but not completely. The muscle mobility of the right mouth angle improved. The hearing increased by 5 dB. After the second course of treatment when closing the right eye, the slit between the lids decreased to 2 mm. The movements of the right mouth angle increased considerably. The headaches were less frequent. In three months, the treatment was repeated and gradually CARBAMAZEPINE® was withdrawn. After the treatment, the palpebral fissure was closing completely, and the movements of the mouth angle were restored. A follow-up examination in six months showed that the hearing improved by 15 dB, and no dysfunction of CN VII was observed.

At this time the patient was pregnant, and she was worried that her condition may affect the functions of CN VII. There were no complications in the course of pregnancy. The patient had check ups every three months. The pregnancy didn't cause any relapse. The delivery was normal.

The MRI showed an insignificant decrease of the cyst.

G. Example VII

(1) Treatment for Minimal Hearing Loss

A group of patients consisting of 56 children was selected. 29 children—4 years of age and 27 children—5-6 years of age.

Minimal hearing disorders were discovered when these children were investigated for speech development delay. The phonemic disturbances were revealed in these patients.

With the signed consent of their parents, the children were treated with ARICEPT®, including 1.25 mg once a day during 20 days. The course of treatment was repeated in three months. Depending on the degree of the impairment and its cause, the patients received from 3 to 8 courses of treatment.

In the children with sensorineural hearing loss, the hearing improved by 5-10 dB.

In the case of combined hearing loss, the improvement was from 5 to 20 dB. The most noticeable improvement of phonemic hearing and speech functions was observed between the 3d and the 5th courses.

Applicant used teaching English as one of the methods of rehabilitation. 15 children at the age of 5-6 years had English lessons. After these lessons, 10 out of 15 children demonstrated a better performance in their native language (Russian and Mari).

Applicant believes that ARICEPT® has a positive effect on establishment and development of speech function. Applicant also observed the improvement of higher psychic functions.

Preliminary results show that alongside the improvement of speech functions and phonemic hearing 85% of the children starting from the 4$^{th}$ course of treatment manifested the increase in the intellect. This observation needs further investigation.

H. Example VIII

(1) Treatment for Sensorineural Hearing Loss of Vascular Genesis

A group of 24 patients at the age of 50-65 were treated for sensorineural hearing loss. The standard therapy didn't give any positive effect and the wearing of a hearing aid increased tinnitus, so the patients opted for treatment with ARICEPT® 2.5 mg twice a day during 25 days. After a 7-10 days break, the course was repeated. After the first course of treatment, 18 patients manifested the decrease of tinnitus. The hearing in one ear improved by 5-10 dB.

6 patients after the treatment complained of irritability and sleep disturbances. So the second intake of the drug at night was withdrawn. After the fourth course of treatment, the patients manifested a slight improvement of hearing. After that, they refused to continue the treatment for the lack of desired effect.

The other 18 patients received ARICEPT® 2.5 mg a day in combination with vasodilating treatment. Three courses of treatment were conducted. The patients manifested improved hearing in one ear and a decrease of dizziness. Then, the patients terminated the treatment because of its high cost.

The invention claimed is:

1. A method for treating sensorineural hearing loss of various genesis, comprising the step of administering an agent, which comprises donepezil hydrochloride (ARICEPT®).

2. The method of claim 1, wherein the donepezil hydrochloride (ARICEPT®) is administered in a dosage of 2.5 mg to 5 mg.

3. The method of claim 2, wherein the donepezil hydrochloride (ARICEPT®) is administered one to two times a day.

4. The method of claim 3, wherein the donepezil hydrochloride (ARICEPT®) is administered in 3 to 15 courses of treatment.

5. The method of claim 4, wherein the donepezil hydrochloride (ARICEPT®) is administered in courses of treatment of 20 to 25 days each.

6. A method for treating sensorineural hearing loss, comprising the step of administering donepezil hydrochloride (ARICEPT®) in a dosage of 2.5 to 5 mg, one to two times a day, for 3 to 5 courses of treatment of 20 to 25 clays each.

7. The method of claim 1, wherein the donepezil hydrochloride (ARICEPT®) is administered in a dosage of 0.625 to 1.5 mg.

8. A method for treating sensorineural hearing loss, comprising the step of administering donepezil hydrochloride (ARICEPT®) in a dosage of 0.625 to 1.25 mg, one to two times a day, for 3 to 15 courses of treatment of 20 to 25 days each.

* * * * *